(12) United States Patent
Stone et al.

(10) Patent No.: US 9,532,775 B2
(45) Date of Patent: Jan. 3, 2017

(54) METHOD AND APPARATUS FOR SUTURE ANCHORS WITH A VERTICAL EYELET

(71) Applicant: Biomet Sports Medicine, LLC, Warsaw, IN (US)

(72) Inventors: Kevin T. Stone, Winona Lake, IN (US); Troy M. Walters, Plymouth, IN (US); Brandon Miller, Rochester, IN (US); Ryan A. Kaiser, Leesburg, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 25 days.

(21) Appl. No.: 13/751,726

(22) Filed: Jan. 28, 2013

(65) Prior Publication Data

US 2013/0138152 A1 May 30, 2013

Related U.S. Application Data

(62) Division of application No. 12/777,690, filed on May 11, 2010, now Pat. No. 8,361,114, which is a division
(Continued)

(51) Int. Cl.
*A61B 17/04* (2006.01)

(52) U.S. Cl.
CPC ...... *A61B 17/0401* (2013.01); *A61B 2017/044* (2013.01); *A61B 2017/0409* (2013.01);
(Continued)

(58) Field of Classification Search
CPC .................... A61B 17/0401; A61B 2017/044; A61B 2017/0445; A61B 2017/0448; A61B 27/0425; A61B 2017/0424; A61B 2017/0422
(Continued)

(56) References Cited

U.S. PATENT DOCUMENTS

| 734,204 | A | 7/1903 | Voss |
| 838,203 | A | 12/1906 | Neil |

(Continued)

FOREIGN PATENT DOCUMENTS

| EP | 0260970 | 3/1988 |
| EP | 0260970 B1 | 7/1995 |

(Continued)

OTHER PUBLICATIONS

Arthrex, Corkscrew Suture Anchors, p. 105 (1998).
(Continued)

*Primary Examiner* — Dianne Dornbusch
(74) *Attorney, Agent, or Firm* — Schwegman Lundberg & Woessner, P.A.

(57) ABSTRACT

A suture anchor operable to secure a suture to a boney tissue. The suture anchor includes a suture-engaging section including a distal end and a proximal end. The distal end is operable to engage the boney tissue and the proximal end is operable to secure the suture. A bone-engaging section is operable to receive at least a portion of the suture engaging section therein. The bone engaging section includes a bone-grasping feature that is operable to engage and secure the bone-engaging section to the boney tissue. The distal end tapers radially outward from a distal tip to define a shoulder that is operable to abut against the bone-engaging section such that when the bone-grasping feature is engaged and secured to the boney tissue, the suture-engaging section is secured and engaged to the boney tissue.

17 Claims, 10 Drawing Sheets

Related U.S. Application Data of application No. 10/612,515, filed on Jul. 2, 2003, now Pat. No. 7,713,285.

(52) U.S. Cl.
CPC .............. *A61B 2017/0412* (2013.01); *A61B 2017/0414* (2013.01); *A61B 2017/0424* (2013.01); *A61B 2090/037* (2016.02)

(58) Field of Classification Search
USPC ...................................................... 606/232
See application file for complete search history.

(56) References Cited

U.S. PATENT DOCUMENTS

| | | | |
|---|---|---|---|
| 2,121,193 A | 6/1938 | Hanicke | |
| 2,268,755 A | 1/1942 | Li | |
| 2,329,398 A | 9/1943 | Duffy | |
| 3,003,155 A | 10/1961 | Mielzynski et al. | |
| 3,845,772 A | 11/1974 | Smith | |
| 3,892,232 A | 7/1975 | Neufeld | |
| 4,275,717 A | 6/1981 | Bolesky | |
| 4,409,974 A | 10/1983 | Freedland | |
| 4,454,875 A | 6/1984 | Pratt et al. | |
| 4,496,468 A | 1/1985 | House et al. | |
| 4,532,926 A | 8/1985 | O'Holla | |
| 4,632,100 A | 12/1986 | Somers et al. | |
| 4,641,652 A | 2/1987 | Hutterer et al. | |
| 4,653,486 A | 3/1987 | Coker | |
| 4,669,473 A | 6/1987 | Richards et al. | |
| 4,738,255 A | 4/1988 | Goble et al. | |
| 4,741,330 A | 5/1988 | Hayhurst | |
| 4,776,328 A | 10/1988 | Frey et al. | |
| 4,779,616 A | 10/1988 | Johnson | |
| 4,836,205 A | 6/1989 | Barrett | |
| 4,895,148 A | 1/1990 | Bays et al. | |
| 4,898,156 A | 2/1990 | Gatturna et al. | |
| 4,899,743 A | 2/1990 | Nicholson et al. | |
| 4,946,468 A | 8/1990 | Li | |
| 4,968,315 A | 11/1990 | Gatturna | |
| 4,994,074 A | 2/1991 | Bezwada et al. | |
| 5,002,550 A | 3/1991 | Li | |
| 5,019,080 A | 5/1991 | Hemer | |
| 5,037,422 A | 8/1991 | Hayhurst et al. | |
| 5,041,129 A | 8/1991 | Hayhurst et al. | |
| 5,064,425 A | 11/1991 | Branemark et al. | |
| 5,100,417 A | 3/1992 | Cerier et al. | |
| 5,120,171 A | 6/1992 | Lasner | |
| 5,122,132 A | 6/1992 | Bremer | |
| 5,127,785 A | 7/1992 | Faucher et al. | |
| 5,141,520 A | 8/1992 | Goble et al. | |
| 5,156,616 A | 10/1992 | Meadows et al. | |
| D331,463 S | 12/1992 | Rosenberg et al. | |
| 5,176,682 A | 1/1993 | Chow | |
| 5,207,679 A | 5/1993 | Li | |
| 5,246,441 A | 9/1993 | Ross et al. | |
| 5,258,016 A | 11/1993 | DiPoto et al. | |
| 5,364,400 A | 11/1994 | Rego, Jr. et al. | |
| 5,370,662 A | 12/1994 | Stone et al. | |
| 5,372,146 A | 12/1994 | Branch | |
| 5,374,270 A | 12/1994 | McGuire et al. | |
| 5,417,712 A | 5/1995 | Whittaker et al. | |
| 5,423,860 A | 6/1995 | Lizardi et al. | |
| 5,431,660 A | 7/1995 | Burke | |
| 5,443,482 A | 8/1995 | Stone et al. | |
| 5,472,452 A | 12/1995 | Trott | |
| 5,520,700 A | 5/1996 | Beyar et al. | |
| 5,522,845 A | 6/1996 | Wenstrom, Jr. | |
| 5,524,946 A | 6/1996 | Thompson | |
| 5,527,342 A * | 6/1996 | Pietrzak et al. | ............ 606/232 |
| D374,287 S | 10/1996 | Goble et al. | |
| D374,482 S | 10/1996 | Goble et al. | |
| 5,562,672 A | 10/1996 | Huebner et al. | |
| 5,573,548 A | 11/1996 | Nazre et al. | |
| 5,584,695 A | 12/1996 | Lal Sachdeva et al. | |
| 5,584,835 A | 12/1996 | Greenfield | |
| 5,584,836 A | 12/1996 | Ballintyn et al. | |
| 5,593,425 A | 1/1997 | Bonutti et al. | |
| 5,601,557 A | 2/1997 | Hayhurst | |
| 5,607,432 A | 3/1997 | Fucci | |
| 5,618,314 A | 4/1997 | Harwin et al. | |
| 5,643,320 A | 7/1997 | Lower et al. | |
| D385,352 S | 10/1997 | Bales et al. | |
| 5,681,352 A | 10/1997 | Clancy, III et al. | |
| 5,683,401 A | 11/1997 | Schmieding et al. | |
| 5,683,418 A | 11/1997 | Luscombe et al. | |
| 5,690,676 A | 11/1997 | DiPoto et al. | |
| 5,720,766 A | 2/1998 | Zang et al. | |
| 5,733,307 A | 3/1998 | Dinsdale | |
| 5,743,914 A | 4/1998 | Skiba | |
| 5,782,864 A | 7/1998 | Lizardi | |
| 5,814,070 A | 9/1998 | Borzone et al. | |
| 5,851,219 A | 12/1998 | Goble et al. | |
| 5,868,789 A | 2/1999 | Huebner | |
| 5,885,294 A | 3/1999 | Pedlick et al. | |
| 5,911,721 A * | 6/1999 | Nicholson ........... A61B 17/0401 606/326 |
| 5,951,560 A | 9/1999 | Simon et al. | |
| 5,957,953 A * | 9/1999 | DiPoto ............... A61B 17/0401 606/232 |
| 5,964,783 A | 10/1999 | Grafton et al. | |
| 5,968,044 A | 10/1999 | Nicholson et al. | |
| 5,980,558 A | 11/1999 | Wiley | |
| 6,045,573 A | 4/2000 | Wenstrom, Jr. et al. | |
| 6,045,574 A | 4/2000 | Thal | |
| 6,059,785 A | 5/2000 | Schavan et al. | |
| 6,086,608 A * | 7/2000 | Ek ...................... A61B 17/0487 606/232 |
| 6,096,060 A | 8/2000 | Fitts et al. | |
| 6,117,162 A | 9/2000 | Schmieding et al. | |
| 6,139,565 A | 10/2000 | Stone et al. | |
| 6,159,235 A | 12/2000 | Kim | |
| 6,168,598 B1 | 1/2001 | Martello | |
| 6,214,031 B1 | 4/2001 | Schmieding et al. | |
| 6,231,606 B1 | 5/2001 | Graf et al. | |
| 6,264,677 B1 | 7/2001 | Simon et al. | |
| 6,287,324 B1 | 9/2001 | Yarnitsky et al. | |
| 6,319,270 B1 | 11/2001 | Grafton et al. | |
| 6,355,043 B1 | 3/2002 | Adam | |
| 6,436,124 B1 | 8/2002 | Anderson et al. | |
| 6,508,830 B2 | 1/2003 | Steiner | |
| 6,517,542 B1 * | 2/2003 | Papay ................ A61B 17/0401 606/232 |
| 6,524,316 B1 | 2/2003 | Nicholson et al. | |
| 6,554,852 B1 | 4/2003 | Oberlander | |
| 6,569,186 B1 | 5/2003 | Winters et al. | |
| 6,648,892 B2 | 11/2003 | Martello | |
| 6,685,728 B2 | 2/2004 | Sinnott et al. | |
| 6,840,953 B2 * | 1/2005 | Martinek ...................... 606/232 |
| 7,172,595 B1 * | 2/2007 | Goble ................ A61B 17/1714 606/86 A |
| 7,517,357 B2 * | 4/2009 | Abrams ............. A61B 17/0401 606/232 |
| 7,713,285 B1 | 5/2010 | Stone et al. | |
| 8,361,114 B2 | 1/2013 | Stone et al. | |
| 2001/0037131 A1 | 11/2001 | Schmieding et al. | |
| 2002/0022840 A1 | 2/2002 | Martello | |
| 2002/0052629 A1 | 5/2002 | Morgan et al. | |
| 2002/0120292 A1 | 8/2002 | Morgan | |
| 2002/0147463 A1 * | 10/2002 | Martinek ........... A61B 17/0401 606/232 |
| 2002/0161401 A1 | 10/2002 | Steiner | |
| 2003/0144696 A1 | 7/2003 | Sinnott et al. | |
| 2004/0230196 A1 | 11/2004 | Martello | |
| 2004/0254580 A1 | 12/2004 | Boock et al. | |

FOREIGN PATENT DOCUMENTS

| | | |
|---|---|---|
| FR | 2 606 270 A1 | 5/1988 |
| GB | 2118474 | 11/1983 |
| WO | WO-8603666 | 7/1986 |

(56) References Cited

FOREIGN PATENT DOCUMENTS

| WO | WO-8901767 | 3/1989 |
|---|---|---|
| WO | WO-8910096 | 11/1989 |
| WO | WO-9314705 | 8/1993 |

OTHER PUBLICATIONS

D-D-sorb Suture Anchor System, ID Innovasive Devices, Inc., A subsidiary of the United States Surgical Corporation (1997).
Cuff Tack Sutureless Fixation Device, Mitek Products, Division of Ethicon, Inc., a Johnson & Johnson company, 2 pages (2001).
U.S. Appl. No. 10/612,515, Examiner Interview Summary mailed Feb. 25, 2009, 4 pgs.
U.S. Appl. No. 10/612,515, Examiner Interview Summary mailed Mar. 6, 2008, 2 pgs.
U.S. Appl. No. 10/612,515, Examiner Interview Summary mailed Jul. 18, 2007, 3 pgs.
U.S. Appl. No. 10/612,515, Examiner Interview Summary mailed Aug. 7, 2009, 4 pgs.
U.S. Appl. No. 10/612,515, Examiner Interview Summary mailed Sep. 18, 2008, 4 pgs.
U.S. Appl. No. 10/612,515, Final Office Action mailed Sep. 28, 2007, 10 pgs.
U.S. Appl. No. 10/612,515, Final Office Action mailed Dec. 19, 2008, 10 pgs.
U.S. Appl. No. 10/612,515, Non Final Office Action mailed Mar. 9, 2007, 9 pgs.
U.S. Appl. No. 10/612,515, Non Final Office Action mailed May 1, 2009, 8 pgs.
U.S. Appl. No. 10/612,515, Non Final Office Action mailed May 23, 2008, 7 pgs.
U.S. Appl. No. 10/612,515, Non Final Office Action mailed Aug. 23, 2006, 14 pgs.
U.S. Appl. No. 10/612,515, Notice of Allowance mailed Dec. 24, 2009, 10 pgs.
U.S. Appl. No. 10/612,515, Response filed Feb. 28, 2008 to Final Office Action mailed Sep. 28, 2007, 20 pgs.
U.S. Appl. No. 10/612,515, Response filed Mar. 19, 2009 to Final Office Action mailed Dec. 19, 2008, 19 pgs.
U.S. Appl. No. 10/612,515, Response filed Jul. 9, 2007 to Non Final Office Action mailed Mar. 9, 2007, 20 pgs.
U.S. Appl. No. 10/612,515, Response filed Jul. 31, 2006 to Restriction Requirement mailed Jun. 29, 2006, 5 pgs.
U.S. Appl. No. 10/612,515, Response filed Sep. 1, 2009 to Non Final Office Action mailed May 1, 2009, 16 pgs.
U.S. Appl. No. 10/612,515, Response filed Sep. 23, 2008 to Non Final Office Action mailed May 23, 2008, 19 pgs.
U.S. Appl. No. 10/612,515, Response filed Dec. 21, 2006 to Non Final Office Action mailed Aug. 23, 2006, 18 pgs.
U.S. Appl. No. 10/612,515, Restriction Requirement mailed Jun. 29, 2006, 6 pgs.
U.S. Appl. No. 10/612,515, Supplemental Response to Non Final Office Action filed Aug. 9, 2007, 13 pgs.
U.S. Appl. No. 12/777,690, Non Final Office Action mailed May 17, 2012, 7 pgs.
U.S. Appl. No. 12/777,690, Notice of Allowance mailed Sep. 20, 2012, 8 pgs.
U.S. Appl. No. 12/777,690, Response filed Aug. 14, 2012 to Non Final Office Action mailed May 17, 2012, 12 pgs.

\* cited by examiner

METHOD AND APPARATUS FOR SUTURE ANCHORS WITH A VERTICAL EYELET

CROSS-REFERENCE TO RELATED APPLICATIONS

This application is a divisional of U.S. patent application Ser. No. 12/777,690 now U.S. Pat. No. 8,361,114 filed May 11, 2010, which is a divisional of U.S. patent application Ser. No. 10/612,515 filed on Jul. 2, 2003, now U.S. Pat. No. 7,713,285 filed May 11, 2010. The entire disclosures of the above applications are incorporated herein by reference.

FIELD

The present invention relates to suture anchors; and particularly to suture anchors including suture eyelets formed to eliminate suture contact with a hole in an anatomy.

BACKGROUND

Surgical or medical procedures are often performed on a body, for example a human body or anatomy, to repair or replace various portions thereof. For example, tendons that attach muscle to bone or ligaments that attach bones to other bones may be replaced for various reasons. For example, an injury to a ligament, such as a ligament in the leg may need to be replaced. Alternatively, the tendon from the muscle may simply be loosened from its attachment point and need to be reattached without the necessity of a replacement.

Regardless of the reason, soft tissues are often fixed to various positions on the bone. For example, to replace a natural tendon fixation point or to replace the tendon itself, fixing a graft to a selected bone area may be desired. One means to fix the soft tissue to the selected area is to provide a suture through a selected portion of the soft tissue and fix the other end of the suture to a selected area on the bone. Various structures can be provided to anchor or hold the suture in the selected bone area.

Although suture anchors do provide a member to fix the suture to a selected portion of a boney portion, it is often desired to provide a suture anchor that is able to substantially protect the suture from engagement with the bone. Generally, suture anchors that are threaded with a suture do not provide complete protection from engagement of the suture with the bone in the bore in which the suture is positioned. This requires greater care and precision while implanting the suture anchor than would otherwise be required.

Also, many suture anchors are substantially difficult to thread or properly engage with the suture. This is particularly the case when the suture must be passed through a substantial portion of the suture anchor. Often, only the eyelets or small bores are the access points to the suture anchor channel, thus limiting the ability to thread the suture through the anchor during a surgical procedure. Therefore, it is also desirable to provide a suture anchor that will provide substantially easy threading of a suture during a surgical procedure.

SUMMARY

A suture anchor to substantially enclose a portion of the suture threaded through the suture anchor and thus to substantially eliminate contact of the suture with the bore into which the suture anchor is positioned. In addition, the suture anchor generally provides for a substantially simple or easy threading of the suture during a surgical procedure. Generally, the suture is provided in a selected end of the suture anchor which is driven into a selected portion of the bone. The suture anchor may either be self-tapping and drilling or may be placed in a pre-drilled or pre-tapped hole.

Generally, the suture anchor includes a bone engaging section having a bone engaging portion such as screw threads, and a suture engaging section, including suture eyelets. A suture passage interconnects the eyelets within the suture engaging section. The suture eyelets and passage are substantially contained within the suture anchor such that the suture that is positioned through the suture anchor does not engage the boney portion but only extends from the suture anchor. Nevertheless, the suture anchor is able to be provided substantially in the boney structure such that substantially no portion of the suture anchor extends above a surface of the boney structure.

According to a first embodiment a suture anchor includes a bone engaging section formed along a bone engaging axis. A bone engaging structure is formed along the bone engaging section and defines a maximum diameter of the suture anchor. A suture engaging section extends from the bone engaging section and defines a diameter less than or equal to the maximum diameter. An eyelet is formed in the suture engaging section to allow a selected portion of a suture to pass through and extend from the suture engaging section generally along the bone engaging axis. A suture passage is defined by the suture engaging section such that the selected portion of the suture remains substantially within the maximum diameter.

According to a further embodiment a method of providing a suture in a suture anchor having a bone engaging section and a suture engaging section with a suture passage formed in the suture engaging section is provided. The method includes providing a first suture passage section extending from a proximal end through a first exterior portion of the suture engaging section. A second suture passage section is provided that extends from the first exterior portion through a second exterior section of the suture passage. Also, a third suture passage section extends from the second suture passage through an exterior portion of the proximal end of the suture engaging section. A suture is passed through the first suture passage section from the proximal exterior through the first exterior portion. The suture is passed from the first exterior portion through the second exterior portion. The suture is also passed from the second exterior portion through the proximal exterior portion.

According to a further embodiment a suture anchor to provide a fixation of a suture in a selected anatomical portion includes an anatomical engaging section having an anatomical engaging portion. A suture engaging section extends from the anatomical engaging section. The suture engaging section defines a first suture eyelet and a second suture eyelet. The suture engaging section defines a suture holding passage interconnecting the first suture eyelet and second suture eyelet and substantially holding a suture relative to the anatomical engaging section. The suture engaging section is adapted to be positioned generally within a selection portion of the selected anatomical portion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses. Although the following is related generally to a suture anchor that can be positioned in a pre-drilled hole, that is a hole provided in the boney structure for acceptance of the suture anchor, it will be understood that a suture anchor including an impacting tip or self-drilling thread may be provided as well. Moreover, it will be understood that the suture anchor, as described and claimed herein, can be used with any appropriate surgical procedure. The various embodiments described herein are merely exemplary and are not intended to be limiting on the claims appended hereto.

Figure 1:
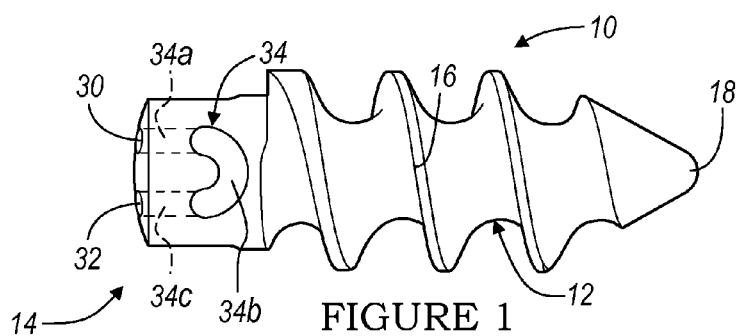
FIG. 1 is a side elevational view of a suture anchor according to an embodiment.
Figure 3:
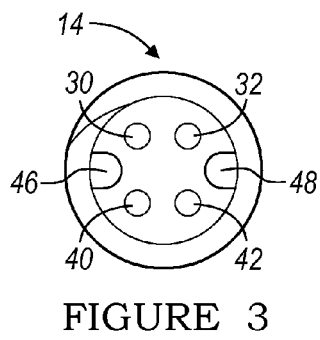
FIG. 3 is a top elevational view of the suture anchor of FIG. 1.
Figure 2:
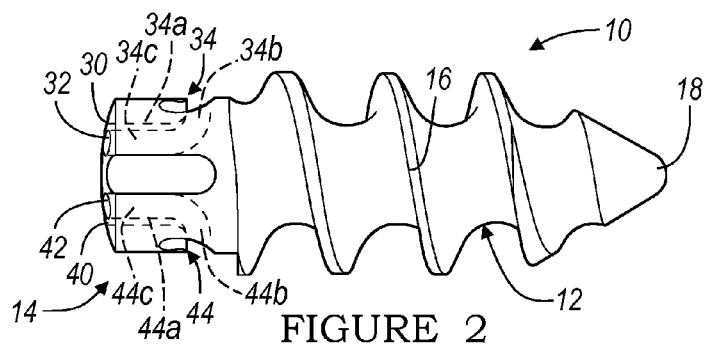
FIG. 2 is a side elevational view of a different side of the suture anchor from FIG. 1.

With reference to FIGS. 1-3, a suture anchor 10 according to an embodiment of the present invention, is illustrated. The suture anchor 10 generally includes a bone engaging or threaded section 12 and a suture engagement or eyelet section 14. Defined along the bone engagement section 12 is a bone engaging structure or portion, such as a thread 16. The thread 16 is able to engage the bone to hold the anchor 10 in a selected position.

The threads 16 may be designed in any appropriate fashion. For example, the threads 16 may include a substantially parallel or planar surface, such as the surface generally facing the suture engagement portion 14 to substantially fix the anchor 10 within the bone. Formed on an end of the bone engaging section 12 is a tip 18 that allows for ease of entry of the anchor 10 into a selected bone portion. The tip 18 may be formed to substantially ease entry of the anchor 10 into the boney portion or may be formed to allow the anchor 10 to be substantially self-drilling or self-tapping. Therefore, the tip 18 may be formed to be substantially sharp or to be any other appropriate design to allow for ease of entry of the anchor 10 into the selected boney portion.

The anchor 10 may be formed of any appropriate material. For example, the anchor 10 may be formed of a polymer, such as polylactic acid exemplary sold by Biomet, Inc. of Warsaw, Ind. as LACTOSORB. Any other appropriate bioabsorbable material may also be used to form the anchor 10. Also, the anchor 10 may be formed of any appropriate bio-compatible material. For example, the suture anchor 10 may be formed of a metal, such as titanium, stainless steel, or alloys of cobalt, chromium, etc. Regardless, the anchor 10 is formed such that it will have a selected pull-out strength to substantially hold the suture anchor 10 in position after the suture anchor 10 has been implanted into the bone.

The suture engaging or eyelet section 14 of the suture anchor 10 includes an area to receive a suture or a portion of a suture. The suture eyelet section 14 includes a first eyelet or bore 30 and a second eyelet or bore 32. Interconnecting the first eyelet 30 and the second eyelet 32 is a suture passage 34. The suture passage 34 includes a first passage portion 34a a second suture passage portion 34b and a third suture passage portion 34c. The suture passage 34 interconnects the first suture eyelet 30 and the second suture eyelet 32. The first suture passage portion 34a interconnects the first eyelet 30 and the second suture passage portion 34b. The third suture passage portion 34c interconnects the second eyelet 32 and the second passage portion 34b. This allows a single suture portion to pass through both the first suture eyelet 30 and the second suture eyelet 32.

The suture eyelet section 14 further includes a third suture eyelet 40 and a fourth suture eyelet 42. The third suture eyelet 40 and the fourth suture eyelet 42 are also interconnected by a suture passage 44. The suture passage 44 includes a first hidden section 44a that extends from the third suture eyelet 40. An exposed or second passage region 44b and finally a third passage region 44c which interconnects with the fourth suture eyelet 42 with the second passage portion 44b. Therefore, the third suture eyelet 40 and the fourth suture eyelet 42 are also interconnected by the second suture passage 44.

As illustrated more clearly herein, a suture may be passed from the first suture eyelet 30 to the second suture eyelet 32 through the first suture passage 34. Similarly, a second suture, or the same suture, but only a different portion thereon, may be passed from the third suture eyelet 40 to the fourth suture eyelet 42 through the second suture passage 44. In the hidden passage regions 34a, 34c, 44a, 44c the suture portion is generally completely contained within the suture eyelet section 14. Similarly the suture is within the boundaries of the suture anchor in the second passage portions 34b, 44b, but the exposed passage regions 34b and 44b allow for visualization of the suture.

Formed in the suture eyelet section 14 is a tool operable portion which includes a first tool operable region 46 and a second tool operable region 48. The first tool operable region 46 and the second tool operable region 48 to allow a tool, such as a forked tool to interact with the suture eyelet section 14 of the suture anchor 10 for insertion of the suture anchor 10 into a boney portion. It will be understood, however, that the suture eyelet section 14 may include any appropriate tool operable design. For example, the suture eyelet section 14 may include a substantially hexagonal perimeter to be received within a substantially hexagonal socket or drive tool. As a further example, various recesses may be formed substantially on the end of the suture eyelet section 14 to be operated by a tool such as a screw driver including a complimentary blade to drive the suture 10 into the selected boney portion. Generally, any appropriate means or device may be used to drive the suture anchor 10 into the selected boney portion.

The suture passage 34 includes the second passage portion 34b that interconnects the first passage portion 34a and the third passage portion 34c. This allows a suture to be passed through the suture engaging section 14 between the first eyelet 30 and the second eyelet 32.

The suture passageways 34, 44 allows for the suture to be substantially contained within the suture engaging section 14 save for when the suture extends from the suture eyelets 30, 32, 40, 42. The suture passageway 34, 44 substantially contains the suture within the suture engaging section 14 such that the bone, into which the suture anchor 10 is positioned, does not easily engage or touch the suture. This decreases the possibility that bone engagement by the suture will harm the suture strength and longevity. Also, the suture passageway 34, 44 allows for containment of the suture only within the suture engaging section 14. Therefore, the suture does not pass through the bone engaging section 12 either before threading of the suture or after implantation of the suture anchor 10 into the bone. Also, the suture eyelets 30, 32, 40, 42 allow the suture to extend from the suture anchor 10 substantially parallel or along an axis of the suture anchor 10. The axis of the suture anchor 10 is generally substantially parallel or along the axis of the bore into which the suture anchor 10 is positioned. Therefore, the suture is able to extend from the suture anchor 10 substantially parallel with the bore formed in the boney portion.

Figure 4:
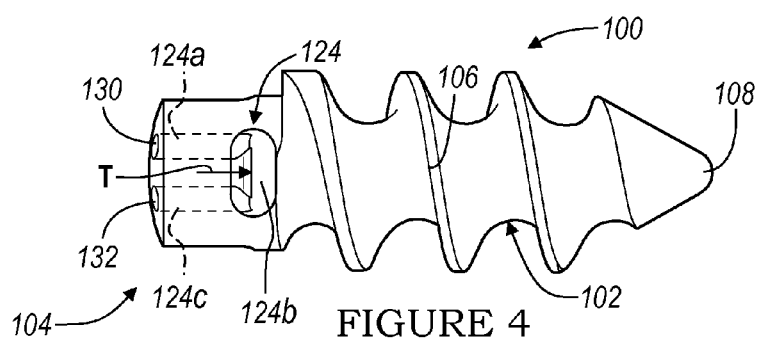
FIG. 4 is a first side elevational view of the suture anchor according to a second embodiment.
Figure 6:
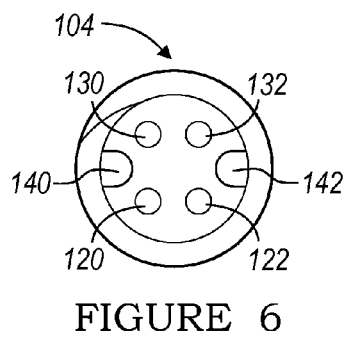
FIG. 6 is a top elevational view of the suture anchor of FIG. 4.
Figure 5:
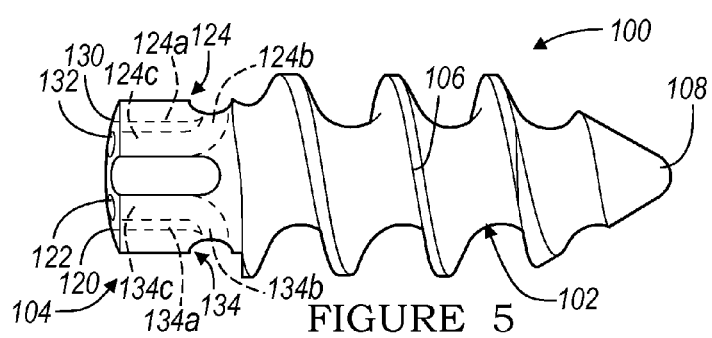
FIG. 5 is a second side elevational view of the suture anchor of FIG. 4.
Figure 8:
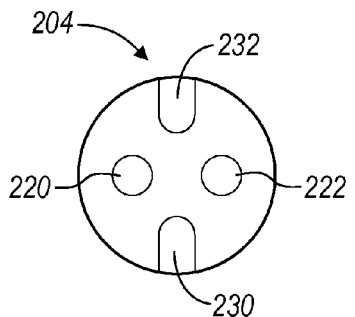
FIG. 8 is a second side elevational view of the suture anchor of FIG. 7.
Figure 7:
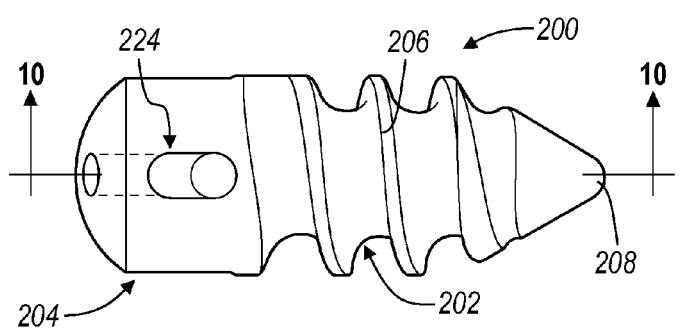
FIG. 7 is a first side elevational view of the suture anchor according to a third embodiment.
Figure 9:
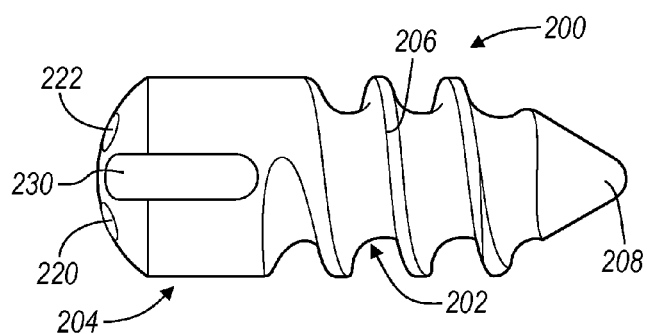
FIG. 9 is a top elevational view of the suture anchor of FIG. 7.
Figure 10:
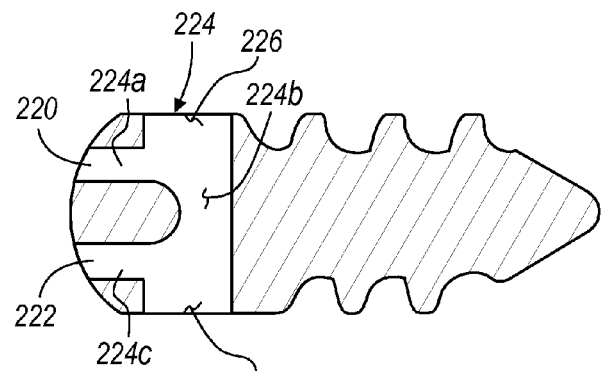
FIG. 10 is a cross-sectional view of the suture anchor of FIG. 8.
Figure 14:
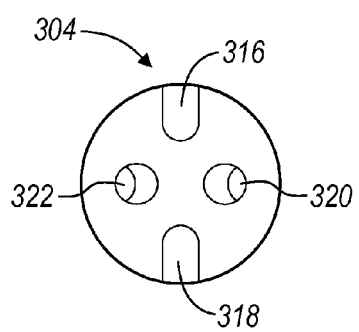
FIG. 14 is a top elevational view of the suture anchor of FIG. 11.
Figure 11:
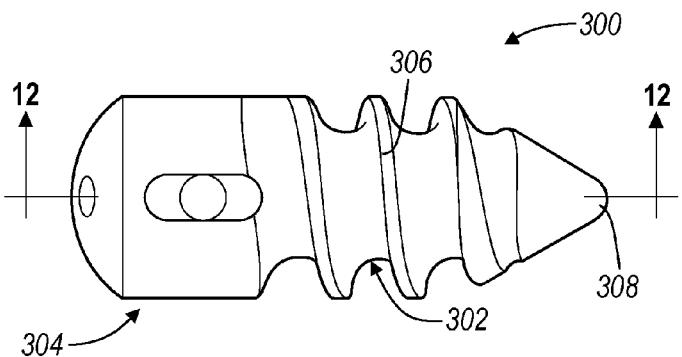
FIG. 11 is a side elevational view of a suture anchor according to a fourth embodiment.
Figure 13:
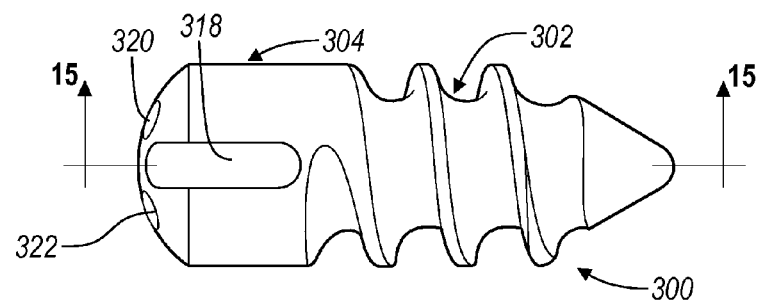
FIG. 13 is a second side elevational view of the suture anchor of FIG. 11.

With reference to FIGS. 4-6, a suture anchor 100 according to a second embodiment is illustrated. The suture anchor 100 is generally similar to the suture anchor 10, described in FIGS. 1-3, save for features that are noted herein. Therefore the description of similar features will be abbreviated. The suture anchor 100 includes a bone engagement or threaded section 102 and extending from the bone engagement section 102 is a suture engagement section 104. Formed on the bone engagement section 102 is bone engaging portion such as a thread 106, although it will be understood that any appropriate bone engaging portion or device may be used to hold the suture anchor 100 in-place. Formed at an end of the bone engaging portion 102 is a tip 108. As discussed above, the tip 108 may be a self-drilling and tapping tip or may simply be a tip to allow for ease of insertion of the suture anchor 100 into the boney portion.

The suture engaging section 104 includes a first suture eyelet 120 and a second suture eyelet 122. The first suture eyelet 120 and the second suture eyelet 122 are interconnected by a suture passage 124. The suture passage 124 includes a first suture passage portion 124a, a second suture passage portion 124b, and a third suture passage portion 124c. The second suture passage portion 124b is generally accessible from the exterior of the suture eyelet section 104. The first suture passage section 124a and the third suture passage section 124c, however, are generally not accessible through the exterior of the suture eyelet section 104, save for through the first suture eyelet 120 and the second suture eyelet 122. Therefore, a suture may be passed from the first suture eyelet 120 to the second suture eyelet 122 through the suture passage 124. Generally, the suture eyelet passage 124 substantially encloses the suture, as described further herein with the first passage portion 124a and the third passage portion 124c. Nevertheless, the suture is substantially viewable and accessible through the open portion 124b of the suture passage 124.

The suture eyelet section further includes a third suture eyelet 130 and a fourth suture eyelet 132. The third suture eyelet 130 and the fourth suture eyelet 132 are also interconnected by a suture passage 134. A first suture passage portion 134a interconnects the first suture eyelet 130 and a second suture passage portion 134b. Extending from the second suture passage portion 134b is a third suture eyelet passage portion 134c. A suture may be passed from the third suture eyelet 130 to the fourth suture eyelet 132 through the second suture passage 134.

The first suture passage 124 including the exposed section 124b generally defines a suture turnaround surface area T. It will be understood that the second suture passage 144 also includes a second suture turnaround area T'. The area of the suture turnaround T can be any selected length or surface area. Moreover, the turnaround T may be formed of any appropriate geometry, that is illustrated exemplary as being substantially parallel with the top of the suture eyelet section 104. As will be discussed further herein, the suture that is passed through the suture passage 124, which the suture anchor 100 anchors relative to a bone portion, generally engages the turnaround area T. Therefore, the turnaround area T, may be any selected surface area to substantially hold the suture in the suture passage 124. Furthermore, it will be understood that the first turnaround T and the second turnaround T' may be different or the same in surface area or size. The surface area or size of the turnaround T, T' may be selected depending upon the suture material chosen, the application of the suture anchor 100 or other appropriate considerations.

Also formed in the suture eyelet section 104 is a first tool operable portion 140 and a second tool operable portion 142. The tool operable portions 140 and 142 are generally able to be operated by a substantially forked tool. The forked tool can transfer a torque from the tool to the suture anchor 100 to allow for insertion of the suture anchor 100 into the boney portion. It will be understood, that any appropriate tool operable portion or geometry may be formed into the suture eyelet section 104. For example, the suture eyelet portion 104 may generally define a hexagonal cross-section to be received within a hexagonal driver.

With reference to FIGS. 7-10, a suture anchor 200 according to a third embodiment is illustrated. The suture anchor 200 is similar to the suture anchor 10 illustrated in FIGS. 1-3 and similar portions thereof will be described in an abbreviated manner. The suture anchor 200 generally includes a bone engaging section 202 and a suture engaging section 204. The bone engaging section 202 is generally able to be driven into a bone by use of a tool.

The bone engaging section 202 includes a bone engaging member or portion such as a thread 206. It will be understood that the thread 206 may be any appropriate bone engaging portion and the thread 206 is merely exemplary. Moreover, the thread 206 may be formed in any appropriate shape or size to engage the bone. At the end of the bone engaging section is a tip 208. The tip 208 allows for ease of entry and engagement of the suture anchor 200 into the selected boney portion. The tip 208 may be substantially sharpened or generally pointed to allow for ease of entering the suture anchor 200 into the bone. Nevertheless, the specific design of the tip 208 may be any selected design to allow for insertion of the suture anchor 200 into the bone. For example, the tip 208 may be designed to allow for easy starting of a self-drilling suture anchor. Similarly, the thread 206 may interact with the tip 208 to allow for ease of a self-tapping or self-drilling suture anchor.

The suture engaging section 204 includes an area to substantially receive a portion of a suture. The suture engagement section generally includes a first eyelet 220 and a second eyelet 222. A suture passage 224 interconnects the first suture eyelet 220 and the second suture eyelet 222. The passage 224 includes a first passage section 224a which extends from the first eyelet 220. A second passage portion 224b that extends from the first passage section 224a and interconnects it with a third section 224c of the suture passage 224. In this way, a suture can be passed from the first eyelet 220 through the suture passage 224 to the second eyelet 222. The second passage section 224b includes a first aperture 226 and a second aperture 228. In this way, the suture positioned in the suture passage 224 can be viewed through the first aperture 226 or the second aperture 228.

The suture engagement section 204 further defines a tool operable area 230 and 232. The tool operable areas 230 and 232 allow for a tool to drive the suture anchor 200 into a selected bone. In this way, the suture anchor 200 can be driven into a bone while a portion of a suture is held within the passage 224.

As illustrated, the suture passage 224 generally allows the suture to be maintained within an exterior wall of the suture anchor 200. Therefore, a suture positioned through the suture passage 224 would generally not be pressed or wedged between the suture anchor 200 and a bone portion as the suture anchor 200 is being driven into the bone.

With reference to FIGS. 11-15, a suture anchor 300, according to a fourth embodiment, is illustrated. The suture anchor 300 generally includes a bone engaging section 302 and a suture engaging section 304. The bone engaging section 302 includes the bone engaging portion, such as a thread 306. It will be understood that the thread 306 is merely exemplary of any appropriate bone engaging portion that can be used to fix the suture anchor 300 in the bone. Extending from an end of the bone engaging section 302 is a tip 308. The tip 308 may be formed in any appropriate manner depending upon the use of the suture anchor 300. The tip 308 may be substantially sharpened and assist in a self-tapping and self-drilling suture anchor. Alternatively, the tip 308 may simply allow ease of insertion of the suture anchor 300 into a pre-drilled hole.

Figure 12:
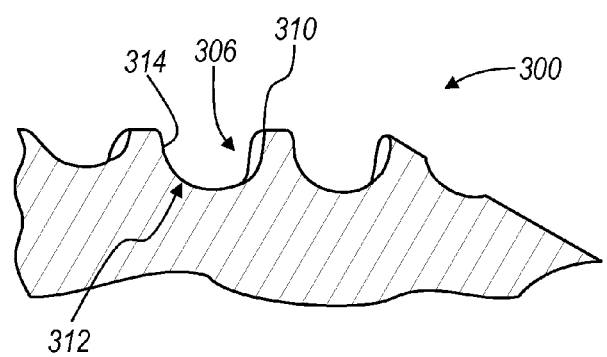
FIG. 12 is a detailed cross-sectional view of the suture anchor of FIG. 11.

With reference to FIG. 12, the thread 306 is formed to allow for substantial fixation of the suture anchor 300 into the bone. For example, the thread 306 may include a substantially planar proximal edge 310. The planar edge 310 assists in holding the suture anchor 300 in the selected portion of the bone. In addition, the thread 306 may define a substantially radius portion 312 extending between the thread 306 turns. A bottom edge 314 of the thread 306 may be formed at an angle relative to the top surface 310 of an adjacent thread. It will be understood, that the thread may be formed in any appropriate manner to allow for fixation of the suture anchor 300 into the bone.

The suture engaging section 304 generally defines a tool operable section including a first tool operable section 316 and a second tool operable section 318. Tool operable sections 316, 318 can be used to allow a tool to transfer torque to the suture anchor 300 to drive the suture anchor 300 into a selected boney portion. It will be understood that any appropriate tool operable section may be formed on the suture anchor 300. For example, the suture engaging section 304 may be formed with a substantial hexagonal cross-section to be driven with a hex driver.

The suture engaging section 304 further defines a first suture eyelet 320 and a second suture eyelet 322. A suture passage 324 interconnects the first suture eyelet 320 and the second suture eyelet 322. Extending from the first suture eyelet 320 is a first suture passage section 324a. The first suture passage 324a extends through an exterior side of the suture engaging section 214 and forms a first suture portal 325a. Extending from the first suture passage 324a, and generally perpendicular to a central axis X of the suture anchor 300 is a second suture passage portion 324b. The second suture passage 324b may be accessed through said first suture portal 325a. Extending from the second suture passage portion 324b and to the second suture eyelet is a third suture passage portion 324c. The second suture passage 324b and the third suture passage 324c also extend through an exterior of the suture engaging section 304 forming a second suture portal 325b. Both the second suture passage 324b and the third suture passage 324c may be accessed through the second suture portal 325b.

The suture passage 324, including the various portions, allows for a suture to be passed from the first suture eyelet 320 to the second suture eyelet 322 and be held substantially within an outside perimeter of the suture anchor 300. In this way, the suture anchor 300 can be implanted into a selected boney portion while containing a suture therein and not binding the suture with the bone during implantation.

The first passage portion 324 is formed generally along an axis A that is formed at an angle to the axis X of the suture anchor 300. Thus the first suture portal 325a is formed on a side of the suture engaging section 304 adjacent the first suture eyelet 320. The second passage portion 324b is formed generally along an axis B that is illustrated outside of the suture anchor 300 for clarity. Furthermore, the third suture passage section 324c is formed generally along a third axis C which is also formed at an angle with the axis X of the suture anchor 300 such that the second suture portal 325b is adjacent the second suture eyelet 322. The first axis A and the second axis B define also define angle α. A congruent angle α' is also defined by the first axis A and the second axis B. Similarly, axis B and axis C define an angle β and a congruent angle β'. The angles formed by the various axes A, B, C generally define the path which is traveled by the suture as it is threaded through the suture anchor 300. The angles α, α', β, β' also define the changes in direction and the degree of bend of the suture passage 324 through its path.

A suture S may be easily threaded through the suture passage 324 by traveling through the various sections of the suture passage. The angles α, α', β, and β' allow for ease of travel of the suture during any threading process, particularly during a surgical procedure. The various angles α, α', β and β' are generally greater than or equal to 90°. These obtuse angles allow the suture to be easily passed through the suture passage 324 during an operative procedure. Moreover, the angles of axis A and C allow the suture to be passed to the exterior of the suture engaging section 304 to ease threading of the suture. For example, the suture anchor 300 may generally be about 5 to about 20 mm long and about 1 to about 5 mm across. Therefore, in this example, the area within the suture engaging portion 304 is substantially small and tight and allows for only minute movements of the suture. Therefore, the suture passage 324 allows for an ease of threading of the suture during any procedure, particularly one being formed by a physician during a surgical procedure.

Figure 15:
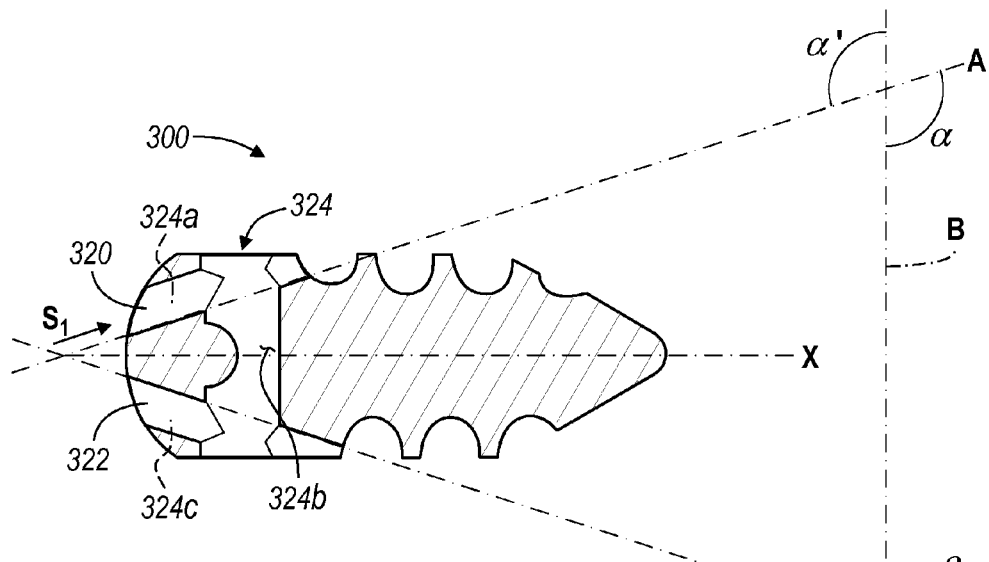
FIG. 15 is a cross-sectional view take along lines 15-15 of FIG. 13.

With particular reference to FIG. 15, an exemplary threading of the suture S is illustrated. The suture S may be passed through the first suture eyelet 320 in the direction of arrow $S_1$. The suture is passed through the first suture eyelet 320 and through the first suture passage portion 324a of the suture passage 324. Generally, the suture may be stiffened or include a needle N on the end being passed through the first suture passage 324. Nevertheless, the suture may be passed through the first suture portal 325a to the exterior of the suture anchor 300 where it may be grasped by an individual. A notch or cutout 326 may be provided to allow for ease of maneuvering of the suture needle N from the first suture passage section 324a to the exterior of the suture anchor.

The needle N, to which the suture S is affixed, may then be turned and passed through first suture portal 325a and the second suture passage section 324b in the direction of the arrow $S_2$ with ease at an angle of at least about 90° and generally greater than about 90°. The second suture passage section 324b generally extends to through an exterior portion of the suture engaging section 304 at the first suture portal 325a. Therefore, the suture needle N and a portion of the suture S can be passed to the exterior of the suture anchor 300. This also allows the suture needle N to be passed from the exterior back through the interior and through the second suture passage portion 324b.

The suture can then be passed through the second side of the suture anchor 300 through the second suture portal 325b. Again, as discussed above, the second suture passage section 324b extends generally through an edge or exterior of the suture anchor 300 at the second suture portal 325b. Once the suture needle N and the portion of the suture S is passed to the exterior of the suture anchor 300 it again gain may be turned to pass through the third suture passage section 324c. A second cutout 328 may be provided adjacent the second passage portion 324b and the second suture portal 325b to allow for ease of maneuvering of the suture needle N during the threading procedure. Nevertheless, the suture needle N and the portion of the suture S can be passed in the direction of the arrow $S_3$ through the third suture passage section 324c and finally out the second suture eyelet 322.

Figures 16A, 16B, 16C:
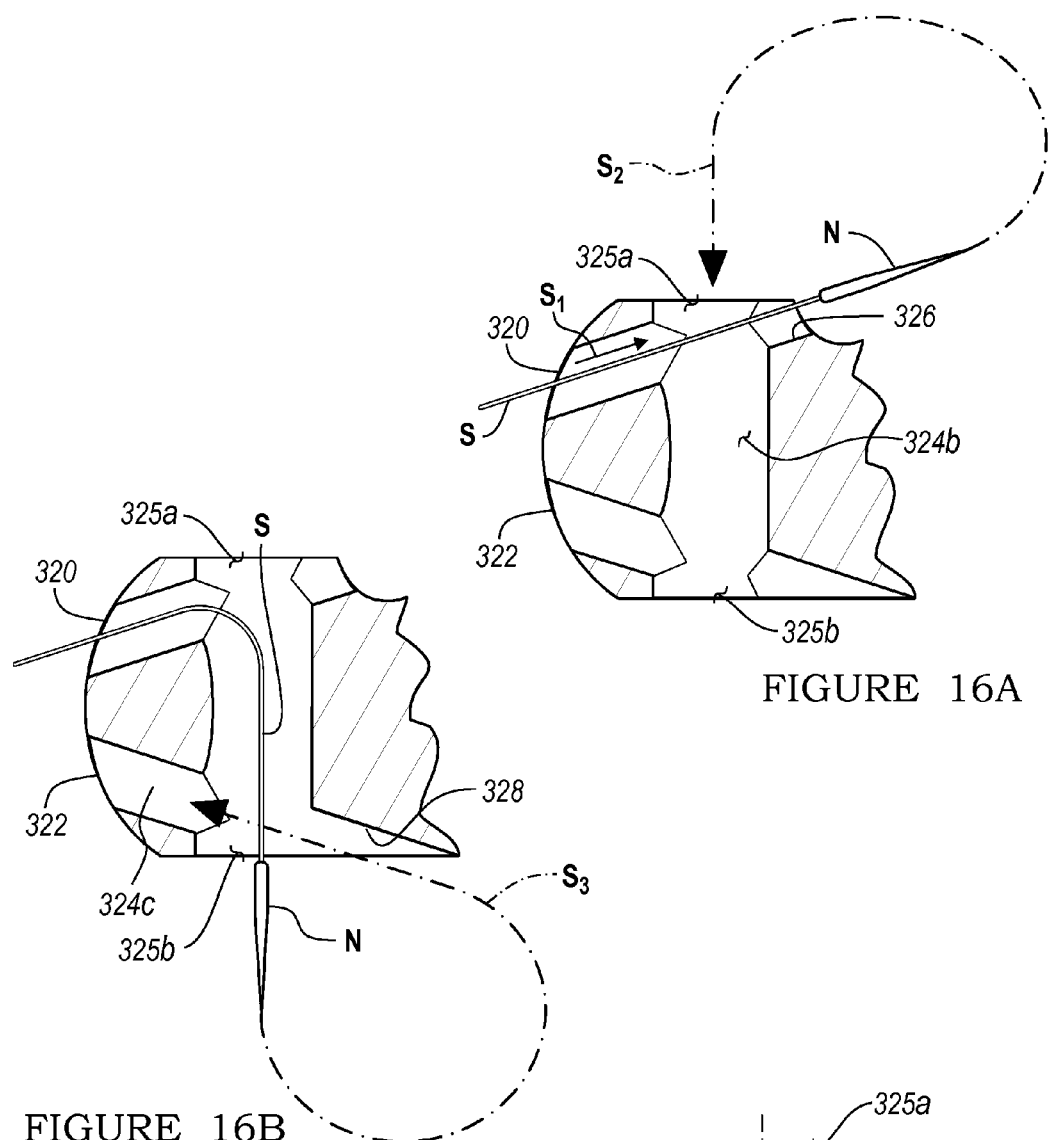
FIG. 16A-16C are a detailed cross-sectional view of the suture engaging section of the suture embodiment of FIG. 15.

Thus, the suture S can be threaded through the suture passage 324 substantially easily without binding of the suture S during the threading procedure. As illustrated particularly in FIG. 16C the suture S, after being threaded through the suture passage 342 does not include any angle less than 90°. As discussed above the suture S is exposed to the angles α, α', β and β' that are all greater than or equal 90°. This allows for a substantially ease and non-binding threading of the suture S through the suture passage 324. These angles also provide that the first suture passage section 324a extends through the first suture portal 325a in the suture engaging section 304 and the third suture passage section 324c extends through the second suture portal 325b in the suture engaging section 304.

Simply, a portion of the suture S which may include a suture needle N may be threaded through the various sections of the suture passage 324 to allow for threading of the suture anchor 300 prior to implantation of the suture anchor 300 into the bone. Also, once the suture S is threaded through the suture anchor 300 substantially no portion of the suture S extends beyond an exterior of the suture anchor 300 save for the portion of the suture S that extends through the eyelets 320, 322. This allows substantially the entire suture anchor 300, including the bone engaging section 302 and the suture engaging portion 304, to be driven into a boney portion to substantially secure the suture S at a selected position.

Figure 17:
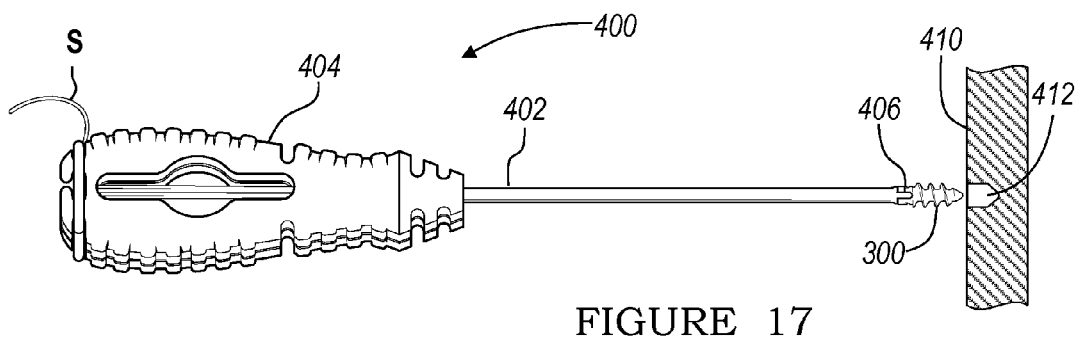
FIG. 17 is an environmental view of a tool engaging a suture anchor according to an embodiment.

With reference to FIG. 17, the suture anchor 300 may be operably implanted into a bone 350 using a tool 360. It will be understood the suture anchor 300 may be implanted in any appropriate manner and the following is simply exemplary. The tool 360 may generally include a cannulated shaft or suture anchor driving portion 362. Extending from the shaft 362 is a handle 364. The handle 364 can be graspable by an individual or may be formed such that it may be grasped by a machine, such as a drill motor or other appropriate driver. The cannulated rod 362 and the handle 364 allow for engagement of a length of the suture S for easy manipulation of the suture after implantation of the suture anchor 300. As exemplary illustrated, the suture driving tool 360 includes a suture anchor fork leg 366 that exemplary allows for the tool 360 to operably drive or manipulate the suture anchor 300. Nevertheless, as discussed above, any appropriate mechanism may be provided to allow for a transfer of a torque and driving force from the tool 360 to the suture anchor 300.

The suture anchor 300 may be threaded and operably positioned adjacent the tool 360 either preoperatively or during the operative procedure. Therefore, it may either be factory loaded or may be loaded by a physician after a choice of a selected suture anchor has been made. A portion of the suture S may be threaded through the suture anchor 300 and passed through the tool 360 to allow for ease of manipulation of the suture anchor 300 during implantation. After the suture anchor 300 is operably associated with the tool 360, a torque and driving force may be provided to the suture anchor 300 to drive it into a selected bone portion 350.

Figure 18:
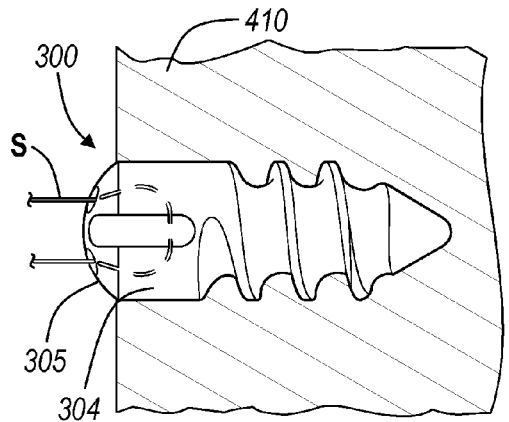
FIG. 18 is a detailed cross-sectional view of a suture anchor engaging a boney portion.

The bone 350 exemplary includes a pre-drilled hole 368 to receive the suture anchor 300. Nevertheless, it will be understood that the bone 350 may be provided without the pre-drilled hole 368 and the suture anchor 300 may be formed to be self-drilling, self-tapping, or an impact type. Nevertheless, the tool 360 allows the suture anchor 300 to be driven into the pre-drilled hole 368. Once the suture anchor 300 is driven into the pre-drilled hole 368, the suture S may be released from the tool 360 and the tool 360 removed from the suture anchor 300. With particular reference to FIG. 18, when fully implanted, the suture anchor 300 is substantially completely received within the bone 410. That is, the outer surface of the bone 350 is generally coplanar with a top 305 of the suture engaging section 304. Thus, the suture anchor 300 does not substantially interrupt the surface of the bone 350.

Disengaging the suture S from the tool 360 frees the tool form the suture anchor 300. It also allows the suture S to be manipulated by the physician during the procedure to substantially anchor any selected portion or graft. For example, the suture anchor 300 may be used to tie down an end of a portion of soft tissue, such as a tendon or ligament.

The suture anchor may be formed of any appropriate material. The suture anchor 300 may be formed of a polymer material, that is either absorbable or non-resorbable, or of a bio-compatible metal. If the suture anchor is formed of an absorbable material, then as the material of the suture anchor is absorbed, bone or biological material may grow into the pre-drilled hole 412. Therefore, a substantially permanent biological fixation of the suture portion or the soft tissue may be formed. Nevertheless, the suture anchor can provide a temporary or permanent fixation of a portion of a suture in an area of a bone that is not included in area that can be easily sutured.

Figure 19:
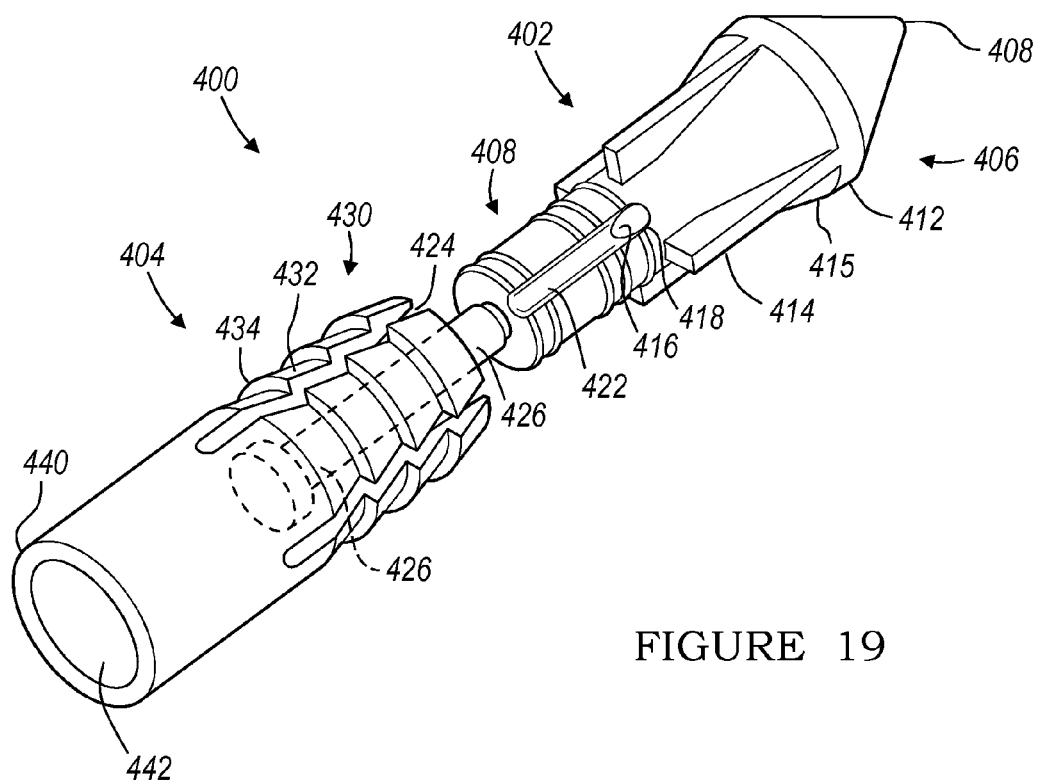
FIG. 19 is an exploded view of a suture anchor according to an alternative embodiment.
Figure 20:
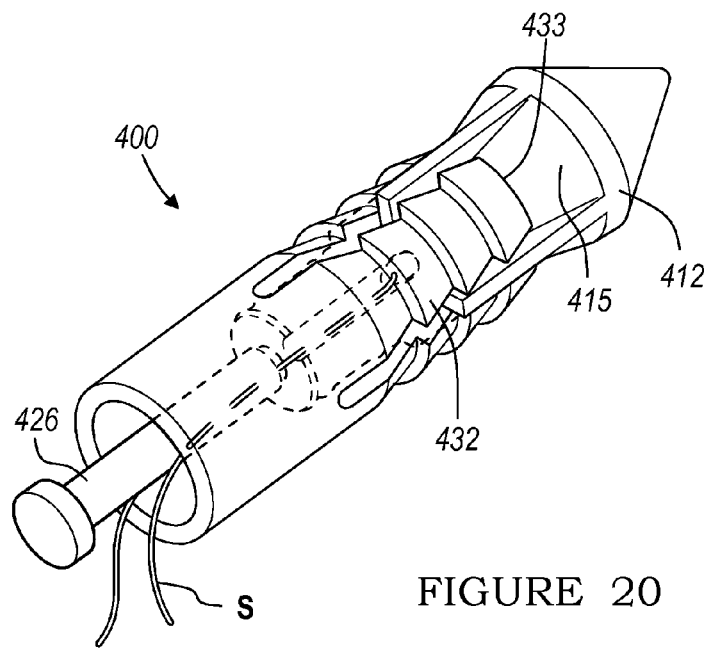
FIG. 20 is an assembled perspective view of the suture anchor of FIG. 19.
Figure 21:
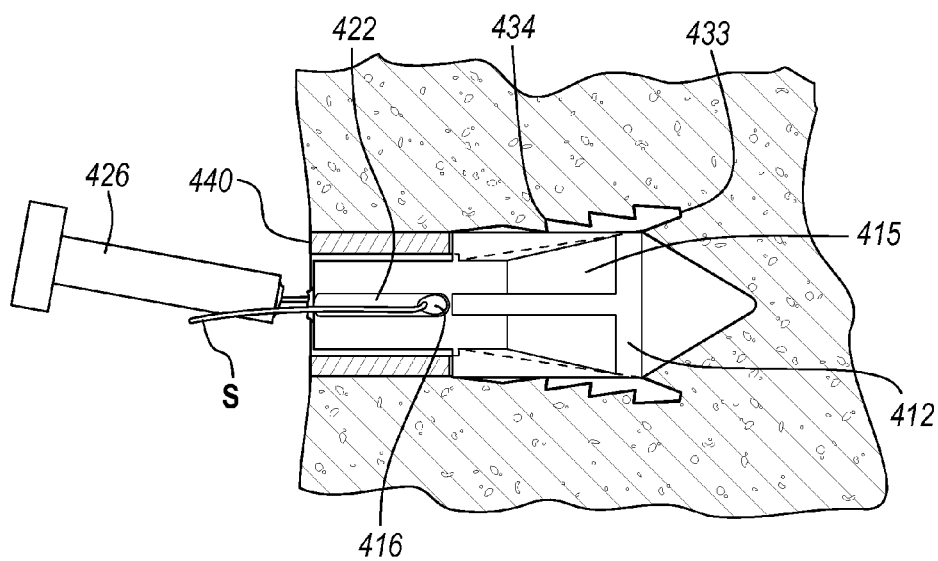
FIG. 21 is a cross-sectional view of the suture anchor of FIG. 19 implanted in a bone.

With reference to FIGS. 19-21, a bone anchor 400 according to an alternative embodiment is illustrated. The bone anchor 400 includes a suture engaging or holding section 402 and a bone or anatomical engaging section 404. The suture engaging section 402 includes a distal tip or expander portion 406 and a proximal eyelet portion 408. The distal end portion 406 exemplary terminates in a tip or point 410 to assist in insertion of the suture anchor 400, as discussed further herein. Nevertheless, for final insertion of the suture anchor 400, the suture engaging section 402 is substantially contained within the bone engaging section 404, as described further herein. The distal end tapers from the tip 410 to a maximum diameter annular ring 412. Extending proximally from the ring 412 is at least one rib or protuberance 414. The protuberance 414 assists in guiding the suture engaging section 402 through the bone engaging section 404 for final implantation of the suture anchor 400.

In the eyelet portion 408 of the suture engaging section 402 is formed a suture eyelet 416. The suture eyelet 416 generally includes a first suture portal 418 and a second suture portal 420. The suture portals 418, 420 allow a suture to be passed through the eyelet 416 to allow for the suture engaging section 402 to hold the suture relative to the suture anchor 400. A first suture passage 421 interconnects the two suture portals 418, 420 to allow a suture to pass through the suture engaging section 408.

Extending from the suture portal 418 towards the proximal end of the suture anchor 400 is a second suture passage 422. The second suture passage 422 allows the suture to be held within an external diameter of the suture engaging section 402. This assists in substantially eliminating or decreasing abrasion of the suture between the suture engaging section 402 and the bone engaging section 404.

Extending proximally from the suture eyelet portion 402 is a pop or setting member 426. The pop section 426 assists in setting the suture anchor 400 within a selected portion of the boney structure, as described further herein. The pop section 426 can be removed from the suture engaging section 402 during or after implantation of the suture anchor 400 into the selected boney portion.

The engaging section 404 includes a distal end 430 and defines at least one deflectable flange or member 432. The flange 432 is deflectable relative to the bone engaging section 404 due to at least a slot 434 defined by the bone engaging section 404. The deflectable member 432 further defines at least a first ridge or bone engaging projection 434. The bone engaging projection 434 assists increasing the pullout strength of the suture anchor 400 after implantation of the suture anchor 400. A distal end 440 of the suture anchor 404 is substantially continuous and can define any appropriate shape. The distal end 440 allows the deflectable members 432 to deflect relative to the bone engaging section 404 while keeping the deflectable members substantially aligned and held relative one another.

With reference to FIGS. 20-21, and preparation of implanting the suture anchor 400, the suture engaging section 402 is pulled into the interior 442 defined by the bone engaging section 404. Prior to pulling the suture engaging portion 404 into the bone engaging portion 402, a suture S is passed through the eyelet 416. The suture S may be held in the second suture passage 422 to limit binding or engagement with the interior 442. This also helps ensure the suture S extends from the proximal end 440 of the bone engaging section 404 substantially vertically or aligned with the suture engaging section 402. The suture engaging section 402 is generally pulled into the interior 442 of the bone engaging section 404 until the proximal taper 415 of the suture engaging section engages a distal end 433 of at least one of the deflectable members 432. This substantially readies the suture anchor 400 to be implanted into a selected boney portion 444.

Generally, the selected boney portion 444 generally includes a bore 446 into which the suture anchor 400 is implanted. The suture anchor 400 is then driven into the bore 446 defined by the bone 444 a selected distance. After the suture anchor 400 is driven into the bore 448 the selected distance, the pop portion 426 is pulled proximally through the interior portion 442 of the bone engaging section 404. This pulls the distal end 406 of the suture engaging section 402 towards the bone engaging section 404. This, in turn, deflects the deflectable members 432 outwardly from the bone engaging section 404. Therefore, the deflectable members 432 further engage the bone and the bone engaging ridges 434 substantially hold the suture anchor 400 in the selected position. At a selected time, the pop section 426 is removed from the suture engaging section 402. At this point, the suture S is substantially held in place as the suture engaging section 402 is locked within the bone engaging section 402 thereby deflecting the deflectable members 432 to engage the bone 444. The distal end 440 of the bone engaging section 404 also protects the suture S from engagement with the bone 444. Therefore, after implantation, the suture S is substantially protected from engagement with the bone 444 to substantially reduce or eliminate wear of the suture S because of movement against the bone 444.

The pop portion 426 can generally be provided to pop or dislocate from the suture engaging section 402 at any selected point. That is, the pop section 426 would generally dislocate or release from the suture engaging section 402 when a selected pressure is formed between the deflectable members 432 and the bone 444. Therefore, a selected holding power of the suture anchor 400 can be determined. Moreover, the pressure created between the deflectable members 432 and the bone 444 can be selected depending upon the selected bone or the condition of the bone into which the suture anchor 400 is implanted.

Figure 22:
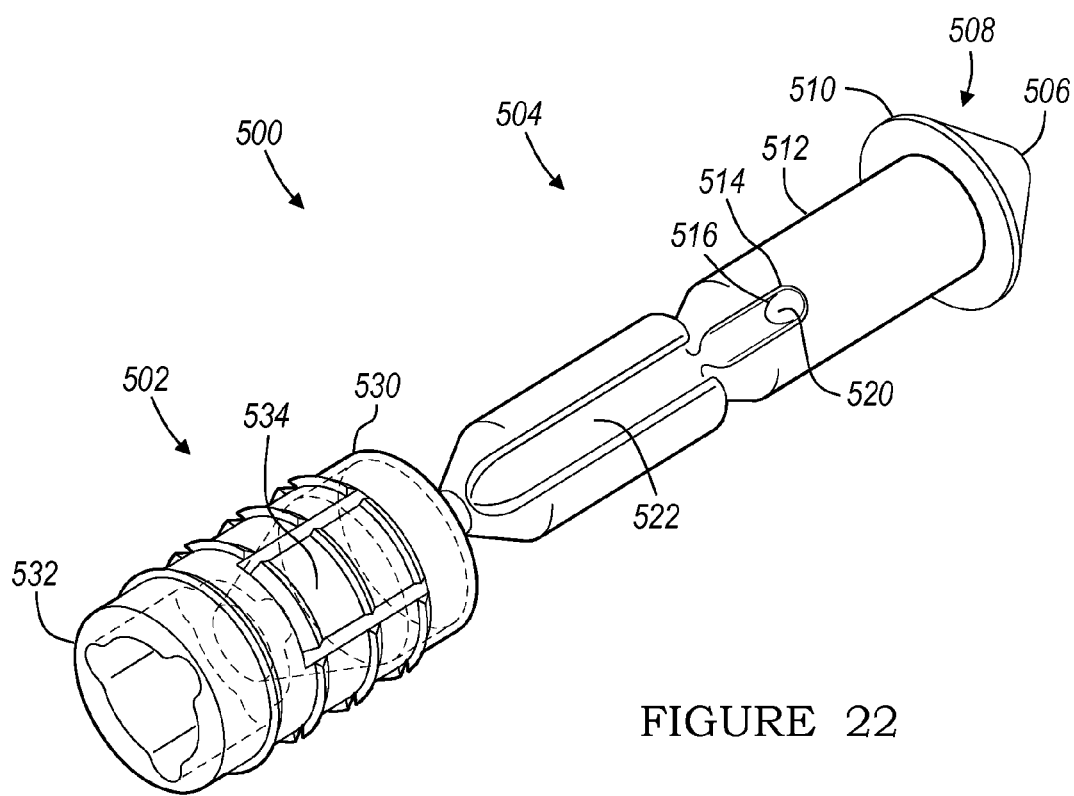
FIG. 22 is an exploded perspective view of a suture anchor according to an alternative embodiment.
Figure 23:
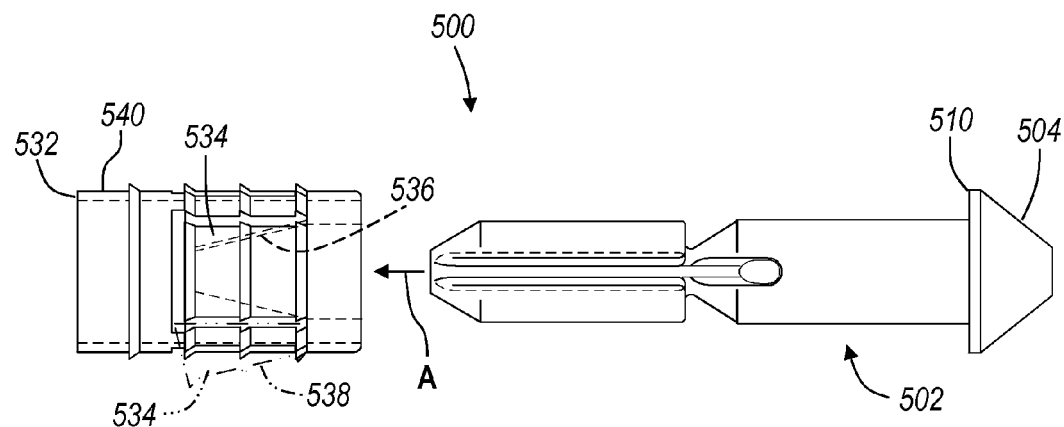
FIG. 23 is an exploded cross-sectional view of a suture anchor of FIG. 22.
Figure 24:
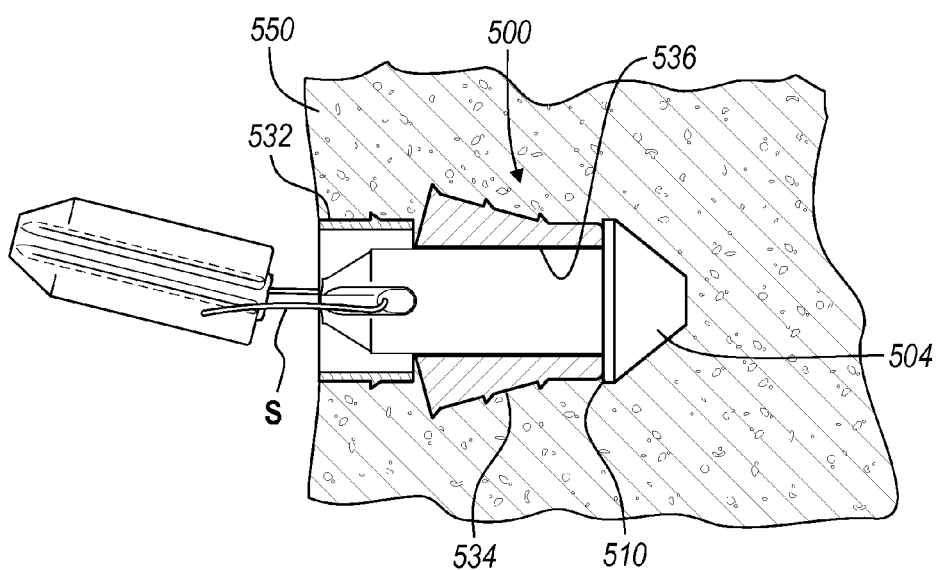
FIG. 24 is a cross-sectional view of the suture anchor of FIG. 22 implanted in a selected portion.

With reference to FIGS. 22-24, a suture anchor 500 according to an alternative embodiment is illustrated. The suture anchor 500 includes a bone engaging section 502 and a suture and expander section 504. The suture anchor 500 is adapted to be able to be driven into a preformed bore in a bone to hold a suture in a selected position. Although it will be understood that the suture anchor 500 may also be driven into an unprepared bone as well.

The suture engaging section 504 includes a distal tip 506 which is an apex of a cone or expander portion 508. The expander portion 508 terminates in a proximal ridge or shoulder 510. Extending further proximally is a suture engaging portion 512 which defines a suture eyelet 514. The suture eyelet 514 includes a first suture portal 516 and a second suture portal 518 to allow a suture to pass through the suture engaging section 512. A suture passage 520 extends between the suture portals 516 and 518 interconnecting them such that the suture can pass through the suture engaging section 512. Extending from each of the portals 516, 518 is a suture guiding path 522. The suture guiding path 522 allows a suture to be held relative to the suture engaging section 512 without engaging the bone engaging section 502 tightly.

The bone engaging section 502 includes a distal end 530 and a proximal end 532. Formed between the distal end 530 and the proximal end 532 is at least a single flexible or deflectable member 534. The flexible member 534 is able to flex or move relative to the bone engaging section 502 to engage a boney portion. The flexible finger 534 includes an interior wall 536 that defines an angle $\alpha$ relative to a plane defined by the proximal end 532. Thus, as the suture engaging expander section 504 is drawn into the bone engaging section 502 in the direction of arrow A, the ridge 510 engages the interior wall 536 and pushes it out as it rides along the wall 536 because of the angle $\alpha$. In turn, this forces an exterior wall 538 of the flexible portion 534 beyond an exterior wall 540 of the proximal end 532. This assists in holding the suture anchor 500 in a boney portion and to substantially hold a suture in place.

With reference to FIG. 24, after the expander portion 502 has been drawn into the bone engaging section 502, the flexible fingers 534 substantially engage a bone 550 into which the suture anchor 500 is implanted. The expander ridge 510 pushes the flexible portions 534 to substantially engage the bone. The suture S which was previously passed through the suture eyelet 514 and drawn through the bone engaging portion 502 is also held in place. Therefore, the suture S is substantially anchored within the bone 550. The bone engaging section 502 defines a buffer or contact area such that the suture S does not engage the bone 550 after implantation of the suture anchor 500. Therefore, the suture S is protected from contact with the hard and rough cortical bone by the suture anchor 500. Also, the internal passage of the suture S through the bone engaging section 502 allows the suture S to extend substantially vertically from the bone 550 and aligned with the suture engaging section 504.

The suture anchor 500 can be formed of any appropriate material, such as a polymer or other suitable biocompatible material such as a metal, for example stainless steel or cobalt chromium alloys. Nevertheless, the suture anchor 500, particularly the bone engaging section 502, is substantially non-abrasive such that contact of the bone engaging section 502 with the suture S does not substantially damage the suture S. Moreover, the suture anchor 500 may be formed of a bio-absorbable material such that over time the suture anchor 500 will absorb into the body leaving the suture S anchored in bone ingrowth growing from the bone 500 or the tissue to which the suture is connected is permanently healed and affixed to a selected bone portion.

Figure 25:
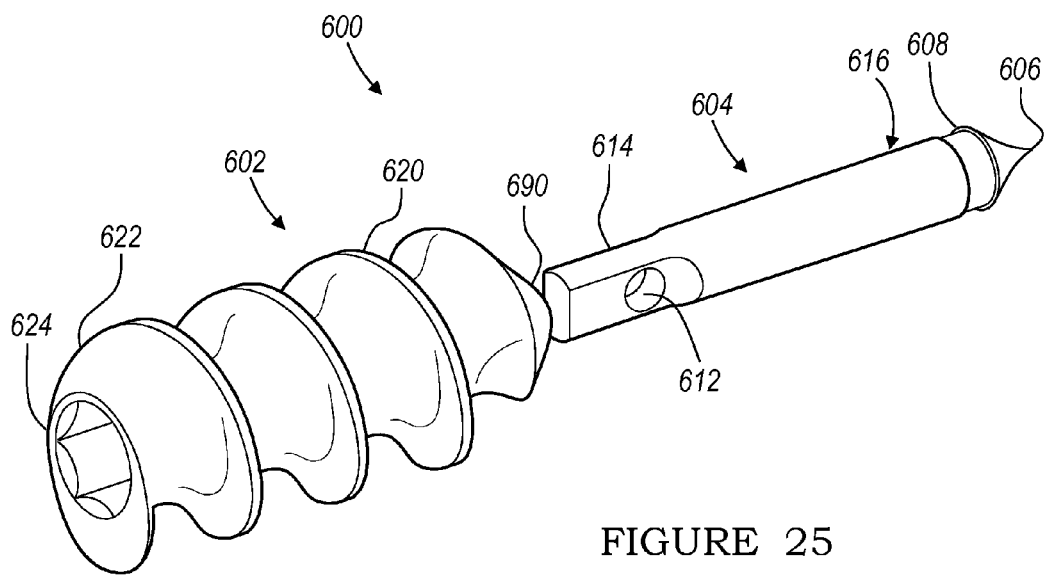
FIG. 25 is an exploded perspective view of a suture anchor according to a further alternative embodiment.
Figure 26:
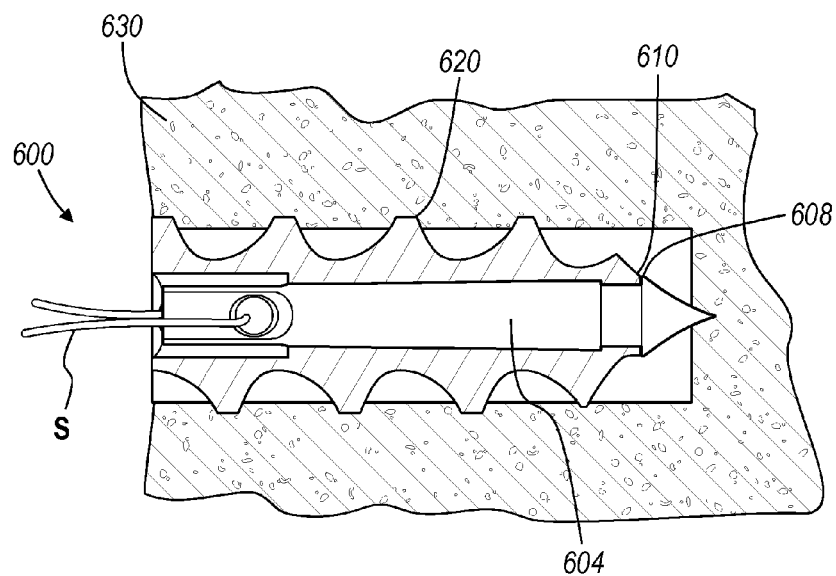
FIG. 26 is a cross-sectional view of the suture anchor of FIG. 25 implanted in a selected portion.

With reference to FIGS. 25-26, a suture anchor 600, according to an alternative embodiment, is illustrated. The suture anchor 600 includes a first or bone engaging section 602 and a second or suture engaging section 604.

The suture engaging section 604 includes a distal end 606 that is substantially pointed to assist in implanting the suture end 600. The suture engaging end 604 tapers to a shoulder or edge portion 608 that includes an external diameter that is greater than an external diameter of a distal end 610 of the bone engaging section 602. As discussed further herein, this allows the suture engaging section 604 to be held firmly by the bone engaging section 602. The distal end 606 of the suture engaging section 604 also assists in driving or piercing through cortical bone. Therefore, the suture anchor 600 can be provided as a self-drilling and self-tamping suture anchor. The distal end 606 can be substantially and tough to easily pierce the cortical bone.

The suture engaging section 604 further defines a suture eyelet 612 through which a suture S may pass. The suture eyelet 612 is positioned in a proximal end 614 of the suture engaging section 604 that includes at least one dimension smaller than a distal portion 616 of the suture engaging section 604. Generally, the suture engaging section 604 may taper smaller from the distal portion 616 to the proximal portion 614. Therefore, the suture that is passed through the suture eyelet 612 does not bind on the bone engaging section 602 as the suture engaging section 604 is passed through the bone engaging section 602.

The bone engaging section 602 defines a bone engaging structure, such as threads 620. The threads 620 may include any appropriate pitch and thread depth to securely engage a bone 630. The bone engaging section 602 further includes a proximal end 622 which defines a tool engaging section 624, such as a hex bore. In this way, a tool may engage the bone engaging section 602 to drive the suture anchor 600 into the bone 630.

The suture engaging section 604 may have a suture S passed through the suture eyelet 612. The suture S can be passed through the bone engaging section 602 through the internal bore and the suture engaging section 604 follow after. The shoulder 608 can then engage the distal end 610 of the bone engaging section 602 to hold it in place as the bone engaging structure 620 engages the bone 630. In this way, the suture engaging section 604 is held substantially in place in the selected portion of the bone 630.

Furthermore, the tool engaging section 624 may have a diameter greater than the proximal end 614 of the suture engaging section such that a cannulated tool may engage the tool engaging bore 624 while not engaging the suture engaging section 604. In this way, the bone engaging section 602 can be rotated while not rotating the suture engaging section 604. The tool may be cannulated such as the sutures may be passed through the tool so that as the tool rotates the bone engaging section 602, the suture S does not become tangled because the suture engaging section 604 does not rotate. The suture engaging section 604 includes the distal shoulder 608 that engages a distal end of the bone engaging section 602 such that driving in the bone engaging section 602 simultaneously drives in the suture engaging section 604. Therefore, the suture anchor 600 allows the suture anchor 600 to be driven into the bone 630 by rotating the bone engaging section 602 and not rotating the suture engaging section 604. It will be understood, however, that both the suture engaging section 604 and the bone engaging section 602 may be simultaneously engaged to insert the suture anchor 600.

The suture anchor 600 can be formed of any appropriate material, such as a polymer or a biocompatible metal such as stainless steel or cobalt chromium alloys. Therefore, the suture anchor 600 can either be self-tapping or self-drilling or screwed into a prepared and tapped bore formed in the bone 630. Nevertheless, according to any formation, the suture S passes from the suture anchor 600 without engaging the bone 630. The suture S is substantially protected from engagement with the bone 630 after implantation of the suture anchor 600 into the bone 630 thereby able to increase the longevity of the suture S. The suture S extends generally aligned with the suture engaging section 604 within the bone engaging section 602 to protect the suture S from engagement with the bone 630. The distal tip 606 can further assist in the self-drilling of the suture anchor 600 by being substantially sharpened or including a self-drilling point.

According to any of the embodiments, an appropriate tool may be used to insert the suture anchor into a selected portion of the bone. Each of the suture anchors 400 and 500 can be pushed into a preformed bore in the bone and the tool used to pull the suture engaging section into the bone engaging section to expand the flexible members to substantially hold the suture engaging section and the bone engaging section relative to the bone.

The suture anchor 600, in addition to the threaded suture anchors 10, 100, 200, and 300 can be drilled or screwed into a selected bone portion. Either the threaded or screwed devices can be self-drilling and tapping or be positioned into a bore which is tapped in the bone. Nevertheless, any of the suture anchors can be appropriately positioned in the bone to hold a suture in a selected position. Nevertheless, each of the suture anchors provides a buffer or protection area to substantially protect the suture S from the bone into which the suture anchor is positioned. The suture extends substantially vertically or axially with the suture anchor such that the suture does not bind or substantially engage the bone surrounding the suture anchor. In this way, the suture is protected from the engagement with the hard cortical bone, generally the bone into which the suture bone is implanted, which may increase the longevity of the suture and decrease the requirements of revision procedures to replace damaged suture.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A suture anchor system, comprising:
   a suture-engaging member including a distal end portion and a proximal end portion, the distal end portion configured to engage a bone or a bone tissue, and the proximal end portion including a suture passage therethrough; and
   a bone-engaging member configured to receive at least a portion of the suture-engaging member;
   wherein, when in a coupled configuration, the bone-engaging member is configured to surround the suture passage and to rotate about the suture-engaging member to allow the suture-engaging member and the bone-engaging member to be contemporaneously driven into a bone or a bone tissue, and the distal end portion of the suture-engaging member tapers radially outward from a distal tip in a proximal direction to define a shoulder that includes an external diameter that is greater than an external diameter of a distal end of the bone-engaging member and that is operable to abut against the distal end of the bone-engaging member.

2. The suture anchor system of claim 1, wherein the bone-engaging member includes a bone-grasping feature and a tool-engaging feature, the tool-engaging feature configured to receive a driver to drive the bone-grasping feature to engage a bone or a bone tissue.

3. The suture anchor system of claim 1, wherein the proximal end portion of the suture-engaging member further includes at least one recess defining a suture guide.

4. A device for securing a suture, comprising:
   a threaded outer sleeve member configured to engage a bone or a bone tissue; and
   a suture anchor, separable from the outer sleeve member and configured to be received within the outer sleeve member, the suture anchor including a distal end and a proximal end, the distal end operable to engage a bone or a bone tissue and tapering radially outward from a distal tip in a proximal direction to define a shoulder that includes an external diameter that is greater than an external diameter of a distal end of the outer sleeve member and that is operable to abut against the distal end of the outer sleeve member, and the proximal end defining a suture engaging portion configured to hold a suture;
   wherein the outer sleeve member is configured to be rotatable relative to the suture anchor when the outer sleeve member and the suture anchor are coupled in a configuration for contemporaneously driving the outer sleeve member and the suture anchor into a bone or a bone tissue.

5. The device of claim 4, wherein the outer sleeve member includes a tool-engaging feature configured to engage with a tool that is configured to drive the device into a bone or a bone tissue by engaging the tool-engaging feature and without engaging the suture anchor.

6. The device of claim 4, wherein the suture engaging portion includes a suture passage section defining a suture passage, the suture engaging portion tapering from the suture passage section to the proximal end of the suture anchor.

7. The device of claim 4, wherein the suture engaging portion includes a suture passage configured to receive the suture, and
   a suture guide path, defined by at least one recess, extending along a length of the suture engaging portion.

8. The device of claim 4, wherein a suture passage of the suture engaging portion is surrounded by the outer sleeve member when the outer sleeve member and the suture anchor are coupled in a configuration for contemporaneously driving the outer sleeve member and the suture anchor into a bone or a bone tissue.

9. A suture anchoring system, comprising:
   a bone engaging member, comprising a proximal end and a distal end, and defining a bore extending at least partially therebetween, the bone engaging member configured to engage a bone or a bone tissue;
   a suture engaging member, comprising a distal end portion and a suture retaining portion, the distal end portion tapering radially outward from a distal tip in a proximal direction to define a shoulder that includes an external diameter that is greater than an external diameter of the distal end of the bone engaging member and that is operable to abut against the distal end of the bone engaging member, and the suture retaining portion extending from the shoulder to a proximal end of the suture engaging member; and
   a suture configured to be retained by the suture engaging member;
   wherein the suture retaining portion is configured to be entirely received within the bore and the bone engaging member is configured to rotate relative to and independently of the suture engaging member when the suture engaging member and the bone engaging member are coupled together in a configuration to contemporaneously drive the bone engaging member and the suture engaging member into a bone or a bone tissue.

10. The system of claim 9, wherein the proximal end of the bone engaging member includes a tool feature configured to engage a tool to drive the bone engaging member into engagement with a bone or a bone tissue.

11. The system of claim 9, wherein the distal end of the bone engaging member is configured to engage the shoulder when the bone engaging member and the suture engaging member are coupled in the configuration to contemporaneously drive the bone engaging member and the suture engaging member into a bone or a bone tissue.

12. The system of claim 9, wherein the distal end portion includes the distal tip configured to pierce a bone or a bone tissue.

13. The system of claim 9, wherein an outer surface of the bone engaging member includes at least one thread configured to permit the bone engaging member to threadedly engage a bone or a bone tissue.

14. The system of claim 9, wherein the suture retaining portion includes a suture passage configured to receive the suture.

15. The system of claim 14, wherein the suture retaining portion further includes at least one recess extending along a length of the suture retaining portion, the at least one recess configured to guide the suture along the length of the suture retaining portion when the suture is coupled to the suture engaging member.

16. The system of claim 9, wherein the suture retaining portion includes a tapered region.

17. The system of claim 16, wherein the tapered region includes a suture passage.

* * * * *